United States Patent [19]

Kingsman et al.

[11] Patent Number: 5,041,385

[45] Date of Patent: Aug. 20, 1991

[54] VECTOR EXPRESSING FUSION PROTEINS AND PARTICLES

[75] Inventors: Alan J. Kingsman; Susan M. Kingsman, both of Islip; Sally E. Adams, Kidlington; Michael H. Malim, Upleadon; Elizabeth-Jane C. Mellor, Oxford, all of United Kingdom

[73] Assignee: Oxford Gene Systems Limited, Oxford, England

[21] Appl. No.: 36,807

[22] Filed: Apr. 10, 1987

[30] Foreign Application Priority Data

Nov. 1, 1986 [GB] United Kingdom ............... 8626148
Apr. 9, 1987 [GB] United Kingdom ............... 8708531

[51] Int. Cl.$^5$ .................. C12N 15/79; C12N 15/11; C12N 15/81; A61K 39/00
[52] U.S. Cl. ........................... 435/320.1; 435/69.3; 435/91; 435/170; 435/181; 435/172.1; 435/172.3; 435/235.1; 435/246.2; 435/252.3; 435/255; 536/27; 424/88; 935/9; 935/12; 935/22; 935/28; 935/59; 935/60; 935/47; 935/69

[58] Field of Search ............... 435/69.3, 91, 170, 171, 435/172.1, 172.3, 235, 240.2, 252.3, 254, 257, 258, 320; 536/27; 424/88; 935/6, 9, 10, 11, 12, 22, 23, 24, 27, 28, 29, 30, 31, 32, 47, 59, 60, 66, 67, 68, 69, 70, 72

[56] References Cited

U.S. PATENT DOCUMENTS 4,722,840 2/1988 Valenzuela et al. ............... 424/88

OTHER PUBLICATIONS

Haynes et al., 1986 (Jul.), Biotechnology 4:637–640.
Mellor et al., 1985, Nature 313:243.
Velenzuela et al., 1985, Bio/Technology 3:323–326.
Wilson et al., 1986, Nucl. Acids Res. 14: 7001–7016.

Primary Examiner—Richard A. Schwartz
Assistant Examiner—Richard C. Peet
Attorney, Agent, or Firm—Allegretti & Witcoff, Ltd.

[57] ABSTRACT

Fusion proteins comprising a first amino acid sequence and a second amino acid sequence are disclosed. The first amino acid sequence is derived from a retrotransposon or an RNA retrovirus and confers on the fusion protein the ability to assemble into particles. The TYA gene of the yeast retrotransposon Ty codes for the first amino acid sequence. The second amino acid sequence is a biologically active antigen. The particles formed by the fusion proteins are useful in vaccines or in diagnostic or purification applications.

2 Claims, 14 Drawing Sheets

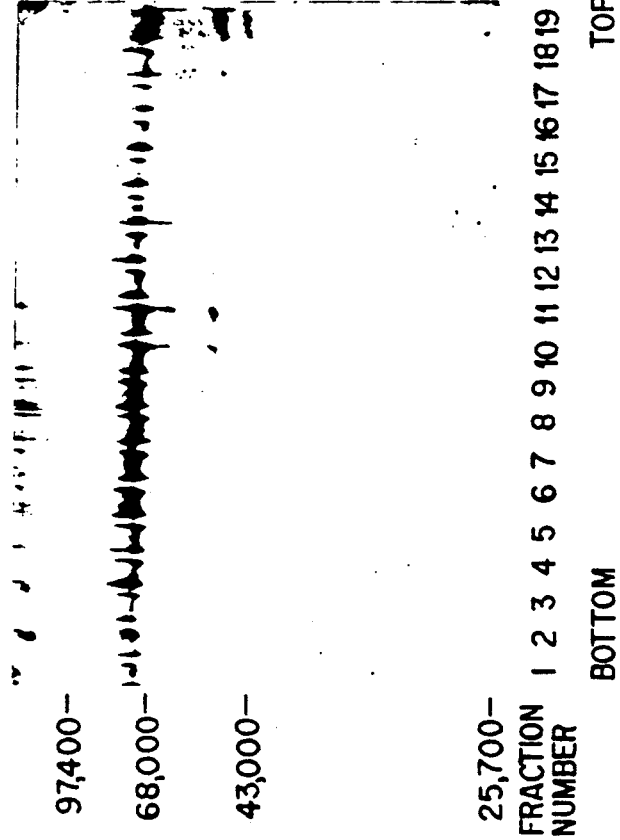
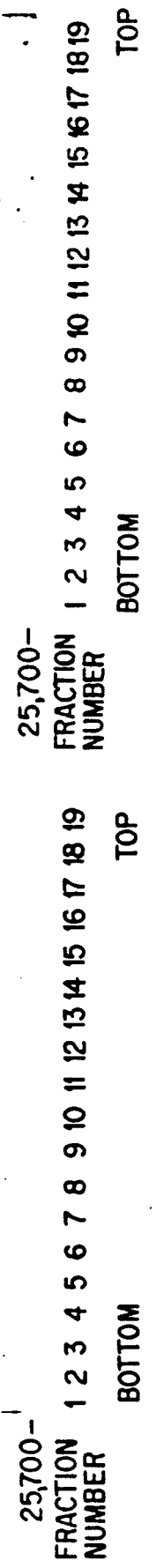
FIG.6a Ty-VLP ANTIBODY
FIG.6b IFN ANTIBODY

FIG. 7

| | 1 | 2 | 3 | |
|---|---|---|---|---|
| | | | | 97K |
| Ty: IFN FUSION PROTEIN | | | | 68K |
| | | | | 25K |

FIG. 9

```
    SpeI
A  CTA GTG AAA ACA ATC ACA AAT GAT CAG ATT GAA
   25              30                      35
   GTG ACT AAT GCT ACT GAG CTG GTT CAG AGT TCC
                   40                  45
   TCA ACG GGG AAA ATA TGC AAC AAT CCT CAT CGA
               50                  55
   ATC CTT GAT GGA ATA GAC TGC ACA CTG ATA GAT
           60                  65
   GCT CTA TTG GGG GAC CCT CAT TGT GAT GGC TTT
       70                  75
   CAA AAT GAG ACA TGG GAC CTT TTC GTT GAA CGC
   80                  85                  90
   AGC AAA GCT TTC AGC AAC TGT TAC CCT TAT GAT
                   95                      100
                                           SpeI
   GTG CCA GAT TAT GCC TCC CTT AGG TTA CTA GT
               105                 110
```

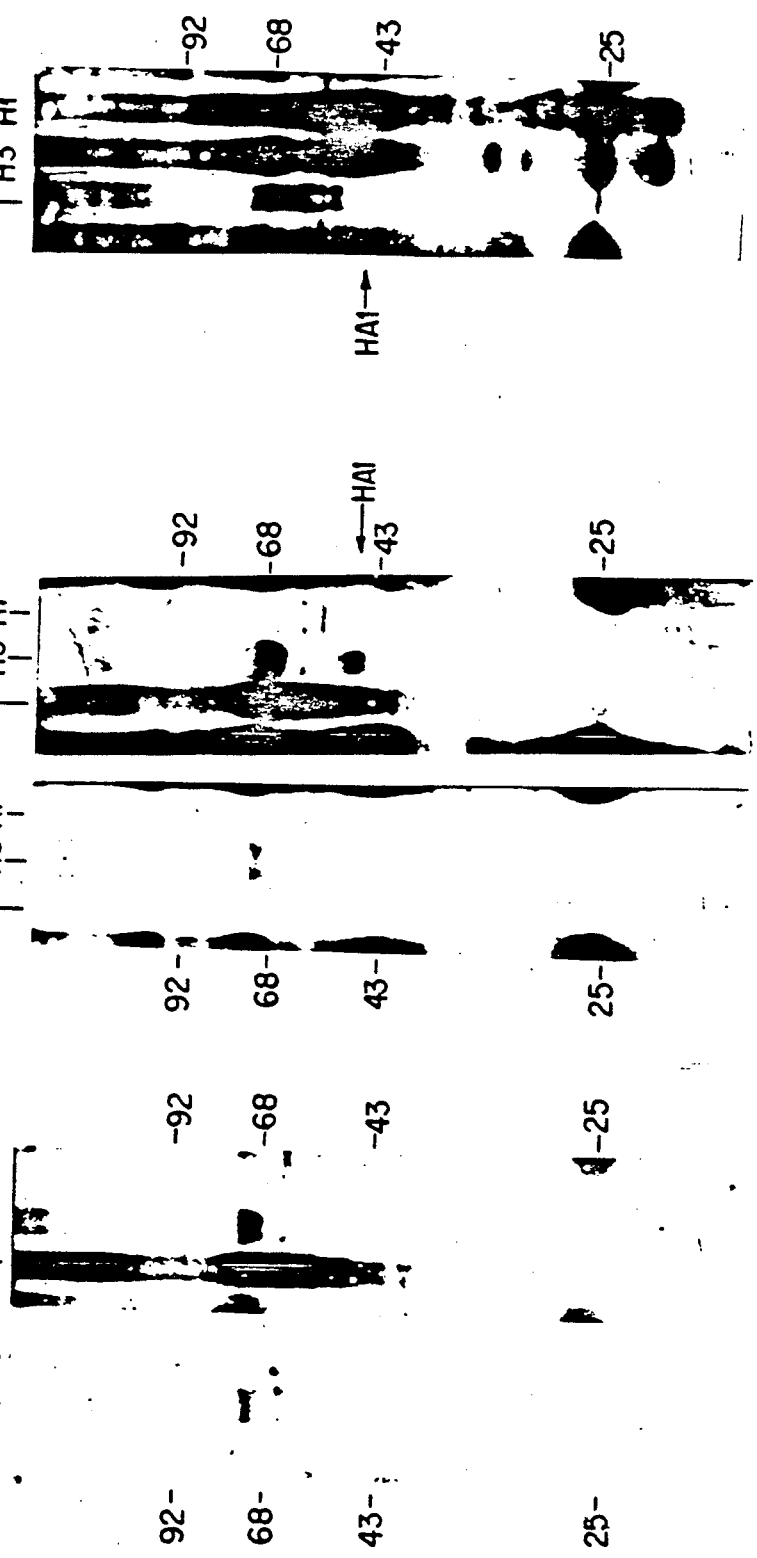

VECTOR EXPRESSING FUSION PROTEINS AND PARTICLES

The present invention relates to an antigen presentation and purification system. In particular embodiments it relates to particles encoded by the yeast retrotransposon Ty, a vector containing the gene for particle formation, a vector for the high level expression of fusions of the particle protein and any antigen and a method for the production and purification of these fusion proteins in yeast.

One of the most important applications of the new recombinant DNA technology is in the production of safe vaccines against infectious diseases and the synthesis of defined proteins against which antisera can be raised for experimental, industrial and diagnostic purposes. Theoretically, these goals can be achieved by the synthesis of appropriate antigens in microorganisms such as the yeast *Saccharomyces cerevisiae*. The antigen would be expressed from an appropriate expression vector (eg European Patent Application EP-A2-0073635).

Correct presentation of the antigen to an animal or human immune system is a key requirement for an effective sub-unit vaccine or immunogen. Presentation has been a major problem with potential vaccines and immunogens made by recombinant DNA as well as for those based on chemically synthesised epitopes. An ideal immunogen is a polymer of multiple antigenic determinants assembled into a high molecular weight carrier. A good immunogen should also have the maximum number of epitopes exposed. These requirements can be difficult to achieve by random chemical coupling of antigens to a carrier. An ideal situation would be where the antigen was presented in the correct conformation on the surface of a large particulate complex. Furthermore the particulate nature of such a system would facilitate the purification of the antigen by simple physical means.

These requirements are rarely achieved by the simple synthesis of monomeric proteins by recombinant DNA technology or chemical syntheses.

Prior to the present invention, the only self-assembling, particulate antigen presentation system for production of immunogens in yeast was based on the fusion of antigens (eg the Herpes Simplex Virus I (HSV-I) glycoprotein D or a Poliovirus antigen) to the Hepatitis B surface antigen (HBsAg) protein via recombinant DNA technology (Valenzuela et al 1985 Biotechnology 3, 323). These fusion proteins aggregate to form 22 nm particles. This system has serious disadvantages: 1) yields are very low; 2) particles do not form in the yeast cell but are a by-product of the extraction process (Hitzeman et al 1983 Nucl. Acids Res. 11,2745). This imposes limitations on the production process; 3) some fusions do not form particles; 4) the HBsAg component exerts immunodominance in some cases, ie antibodies are made preferentially to HBsAg.

Kniskern et al in *Gene* 46 135 (1986) have reported that Hepatitis B core antigen (HBcAg) forms particles in yeast at very high levels, but there has been no published report of its use to carry other epitopes. As these particles are reported to be highly immunogenic in mice they may exert immunodominance like the HBsAg particles.

A corresponding system in bacteria has been reported by Haynes et al (Bio/Technology 4 637 1986). Tobacco mosaic virus (TMV) coat protein is the entity which assembles. When the TMV coat protein is expressed in *E. coli* and then purified it is possible to assemble the proteins into polyvalent particles in vitro. Fusion proteins made from TMV coat protein and another protein may produce hybrid particles that are immunogenic. A polio epitope of only eight amino acids has been tested and shown to be immunogenic although it was four times less immunogenic than the Salk vaccine. This system has the potential advantages that the size of the particle may be varied experimentally and mixed particles (ie carrying more than one type of epitope) could possibly be easy to produce. However, an anticipated disadvantage is that only relatively small antigens will be able to be added to the TMV particle.

Mellor et al in Nature 313 243 (1985) disclose a fusion protein comprising the product of a yeast Ty open reading frame ORF1 (now designated the TYA gene), an open reading frame ORF2 (now designated the TYB gene) and nucleic acid coding for interferon. However, there is no disclosure or suggestion in this paper that the fusion proteins produced, or indeed any Ty protein, are or might be capable of assembling into particles.

It has now been discovered that certain proteins expressed by the genetic material of retrotransposons have the ability of self-assembling into particles. It has also been discovered that it is possible to construct fusion proteins, based on such retrotransposon-derived assembling proteins, which can assemble into antigen- (or other biologically active molecule-) presenting particles. A further discovery that has been made is that similar fusion proteins can be constructed based on RNA retrovirally-derived assembling proteins.

According to a first aspect, the present invention provides a fusion protein capable of assembling into a particle, the fusion protein comprising a first amino acid sequence and a biologically active second amino acid sequence, wherein the first amino acid sequence is substantially homologous with a particle-forming protein encoded by a retrotransposon or an RNA retrovirus and wherein, if the second amino acid sequence contains more than thirty amino acid residues, the first thirty residues of the second amino acid sequence do not form an amino acid sequence naturally directly fused to the first amino acid sequence by the said retrotransposon or RNA retrovirus.

According to a second aspect, the invention provides a particle comprising a plurality of fusion proteins, each fusion protein comprising a first amino acid sequence and a second amino acid sequence, wherein the first amino acid sequence is substantially homologous with a particle-forming protein encoded by a retrotransposon or an RNA retrovirus and wherein the second amino acid sequence is biologically active and not naturally fused to the first amino acid sequence by the said retrotransposon or RNA retrovirus.

Such particles will generally be substantially pure, by which is meant at least 5%, 10%, 20%, 50%, 80%, 90%, 95% or 99% by weight pure, in increasing order of preference.

A given particle may be composed of a plurality of different fusion proteins; that is to say fusion proteins having different second amino acid sequences from each other. Two, three or even more different second amino acid sequences may be present in a particle.

The first amino acid sequence may be the product of the yeast Ty TYA gene, the product of copia and copia-like elements from insects or the gag gene of RNA retroviruses.

Retroviruses include Human Immunodeficiency Virus I and II (HIV-I, HIV-II), Human T-cell Lymphotrophic Virus I and II (HTLV-I, HTLV-II), Murine Leukaemia Virus, Moloney Murine Leukaemia Virus, Mouse Mammary Tumour Virus, Avian Leukosis Virus, Feline Leukaemia Virus, Human B-cell Lymphotrophic Virus, and Bovine Leukaemia Virus. Retrotransposons, as indicated above, include the Ty element of yeast, the and copia-like copia elements of insects such as Drosophilia melanogaster, VL30 in mice and IAP genes in mice.

Preferred retrotransposons include the yeast retrotransposon Ty. It has previously been shown that Ty directs the synthesis of 60nm virus-like particles (Ty-VLPs) (Mellor et al 1985a Nature 318, 513). It has now been discovered that the p1 protein, encoded by the TYA gene is stable and does not appear to require further processing. Therefore the Ty-encoded amino acid sequence is preferably the p1 protein encoded by the TYA gene. It is known (Fulton et al NAR 13(11) 1985 4097) that both classes (I and II) of Ty make p1; so either class may be used.

The Ty-encoded amino acid sequence need not be the whole of the p1 protein; instead it may be a part of the p1 protein encoded by a part of the TYA gene, which part is capable of directing the synthesis of Ty virus-like particles (Ty-VLPs). Preferably the Ty-encoded amino acid sequence is derivable from Ty1-15. The stop codon at the end of the TYA gene is preferably not included; if it is included, however, fusion protein may continue to be expressed, albeit at low yield, as it appears that the stop codon may be ignored with a frequency of about 1 in 20 times by the frameshifting mechanism described by Wilson et al (NAR 14(17) 1986 7001).

It is therefore now shown, among other things, that Ty protein p1, the product of the TYA gene (Dobson et al 1984 EMBO.J 3, 1115) is sufficient to produce Ty-VLPs.

The second amino acid sequence (ie in particular embodiments the non-Ty protein coding region) could be any amino acid sequence either known to the art or yet to be elucidated. The biological activity may be a single type of activity (for example antigenicity, receptor binding activity, therapeutic activity or targeting activity (ie the ability to home to a particular target)) or it may have a combination of two or more different biological activities. Equally, different fusion proteins may assemble into a particulate antigen, thereby causing the whole particle to have more than one activity.

As an example the second amino acid sequence may be derived from a lymphokine gene such as an interferon gene, or a gene coding for an antigen of an infectious agent such as a virus, bacterium or other (eg protozoal) parasite. For example, it may be an influenza virus, an HIV-I or HIV-II (ie HTLV-III, LAV or AIDS) virus, a rabies virus, FMDV virus, HBsAg, HBcAg, polio virus, influenza virus, parainfluenza virus, respiratory syncytial virus, rhinovirus, coronavirus, adenovirus, Rotaviruses, Norwalkviruses, Arboviruses eg Dengue, Herpes simplex, Cytomegalovirus, Epstein Barr virus, Measles virus, Mumps virus, Rubella, Equine influenza virus, Equine rhinopneumonitis, Swine transmissible gastroenteritis virus, Distemper, Parvovirus, FeLV, Venezuelan or Western equine encephalitis, plasmodium, trypanosome, Schistosomes, Chlamydia trachomatis or a meningococcus or it may be a chemically synthesised coding sequence.

A first part of the second amino acid sequence may be a linker sequence, which may in some circumstances be readily cleavable. The remainder of the second amino acid sequence may thus be cleaved off in a purification step.

Particulate antigens in accordance with the invention may therefore be useful in the preparation of vaccines, which form a further aspect of the invention. The second amino acid sequence may thus code for an amino acid sequence of an antigen of one of the above infectious agents. The vaccine may comprise a particulate antigen and a physiologically acceptable non-toxic carrier, such as sterile physiological saline or sterile PBS. Sterility will generally be essential for parenterally administrable vaccines. One or more appropriate adjuvants may also be present. Examples of suitable adjuvants include muramyl dipeptide, aluminium hydroxide and saponin.

It should be noted that vaccines in accordance with the invention may present more than one antigen. Either a cocktail of different particulate antigens may be used, or a homogeneous population of particulate antigens having more than one epitope could be used (prepared, for example, by allowing a mixture of different hybrid proteins to aggregate into particles or by expessing more than one particulate antigen in the same cell); alternatively, a vaccine could contain a mixture of these sorts of particulate antigens.

In a further aspect, the invention provides nucleic acid comprising a first nucleotide sequence and a second nucleotide sequence, wherein the first nucleotide sequence is substantially homologous with or complementary to genetic material in a retrotransposon or RNA retrovirus encoding a particle-forming protein, and wherein the second nucleotide sequence encodes, or is complementary to a nucleotide sequence which encodes, another, biologically active, amino acid sequence, the nucleic acid being capable of being expressed in a single reading frame to form a fusion protein which is not naturally produced by the said retrotransposon or RNA retrovirus.

It will generally be the case that the nucleic acid will be capable of being expressed without splicing or antitermination events. There will generally be no frameshifting.

In certain embodiments of the invention, we provide a TYA gene derivative that can be fused to any non-Ty protein coding sequence to produce a TYA fusion gene. The TYA fusion gene produces a fusion protein that assembles into hybrid Ty-VLPs. These hybrid Ty-VLPs constitute a high molecular weight particulate antigen (or other particle) presentation system that can be produced in very high yields and that can be purified by simple physical procedures.

Further according to the present invention we provide an expression vector including nucleic acid as defined above. An example is pMA5620, which includes the TYA gene derivative, and which directs the high level production of hybrid Ty-VLPs in yeast.

Expression vectors in accordance with the invention will usually contain a promoter. PGK is a preferred promoter, but any other promoter may be used if necessary or desirable. Examples include GAPD, GAL1-10, PHO5, ADH1, CYC1, Ty delta sequence, PYK and hybrid promoters made from components from more than one promoter (such as those listed).

The invention also includes host cells (for example yeast or animal cells) containing (eg the above) expression vectors.

Because of the polyvalent nature of the particulate antigens it is likely that it will be easier to produce antibodies than with conventional antigens and that those antibodies will have specific characteristics. The invention thus further provides antibodies raised against particles of the invention which are antigenic. The antibodies may be polyclonal (obtained for example by injecting antigens into a rabbit) or monoclonal antibodies, produced by hybridoma cells in accordance with the invention. Because of the polyvalent nature of the particulate antigens it is likely that in vitro immunisation can be achieved more readily than with other forms of antigen; this may facilitate the production of human monoclonal antibodies. Hybridoma cells may be prepared by fusing spleen cells from an immunised animal with tumour cell. Appropriately secreting hybridoma cells may thereafter be selected. (See Koehler & Milstein Nature 1976 296 495.)

The invention also provides a suitable technique for purifying biologically active peptides. This aspect of the invention is based on the fact that it is generally relatively easy to separate particles from associated impurities (for example by filtration of centrifugation). Therefore, there is also provided a method of producing a substantially pure biologically active peptide the method comprising separating particles as described above from associated impurities and subsequently cleaving biologically active peptide from the fusion proteins of the particles.

The invention is now illustrated by the following Examples, with reference to the accompanying drawings, in which:

FIG. 6 shows photographs of Western blots of the sucrose gradient fractions from extracts of MD40-4c containing pMA5620-8. a) shows the result using anti Ty-VLP antibody; b) shows the results using anti interferon antibody.

FIG. 7 shows a photograph of Coomassie stained SDS polyacrylamide gel analyses of proteins in the purified hybrid Ty:IFN-VLP preparation (1) and total extracts of MD40-4c transformed with pMA5620-8 (2) and untransformed MD40-4c (3).

Figure 8:
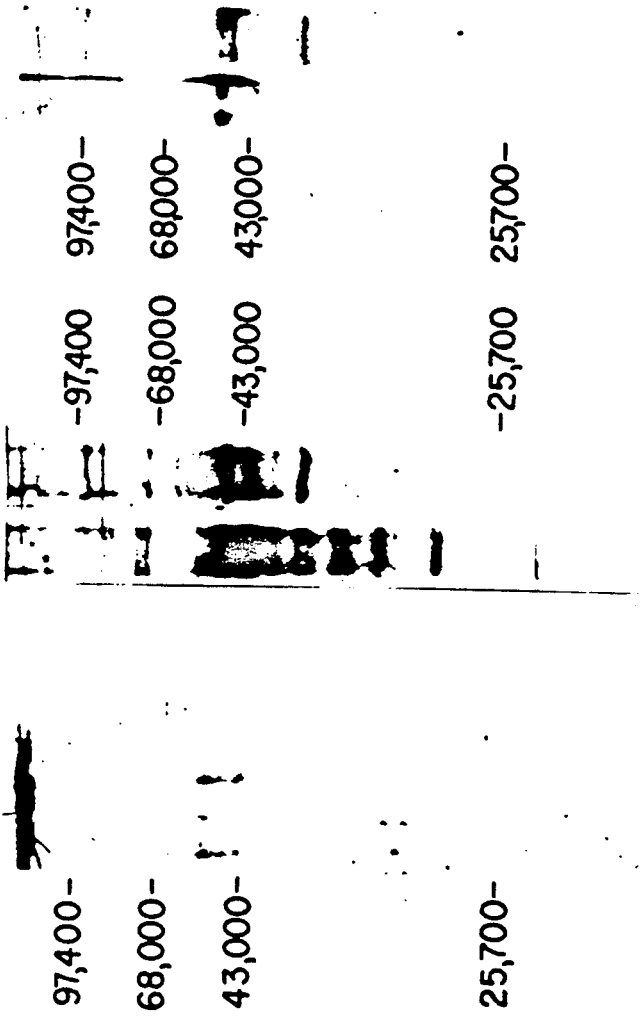

FIG. 8 (A,B,C,D) shows photographs of Western blots using anti Ty-VLP antibody (b), anti hybrid Ty-:IFN-VLP antibody (d) and the corresponding 'prebleed' sera (a+c). Each is used against total extracts of MD40-4c containing pMA91 (1) and pMA91-1 (2). Plasmid pMA91-1 directs the synthesis of IFN-alpha2. pMA91 is a negative control, producing no interferon.

FIG. 9 shows the nucleotide sequence of the 262 bp SpeI:SpeI fragment containing HA codons 25-111, referred to in Example 5.

Figure 10:
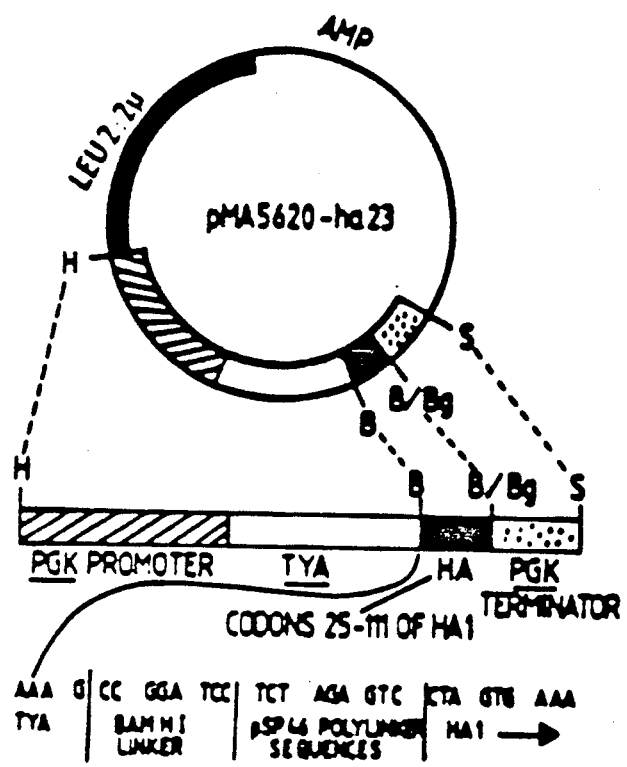

FIG. 10 shows a diagram of plasmid pMA5620-ha23.

Figure 11A:
Figure 11B:
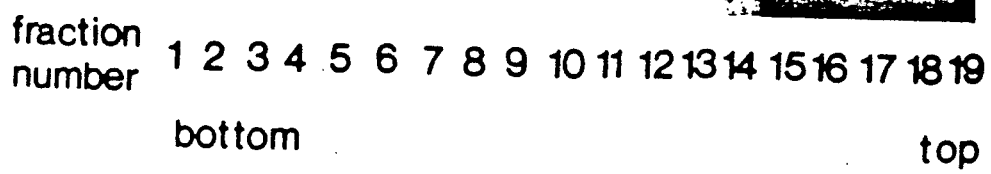

FIG. 11 (A,B) shows an SDS-PAGE analysis of sucrose gradient fractions of extracts of MD40-4c transformed with pMA5620 or pMA5620-ha23. Proteins are stained with Coomassie blue.

Figure 12:
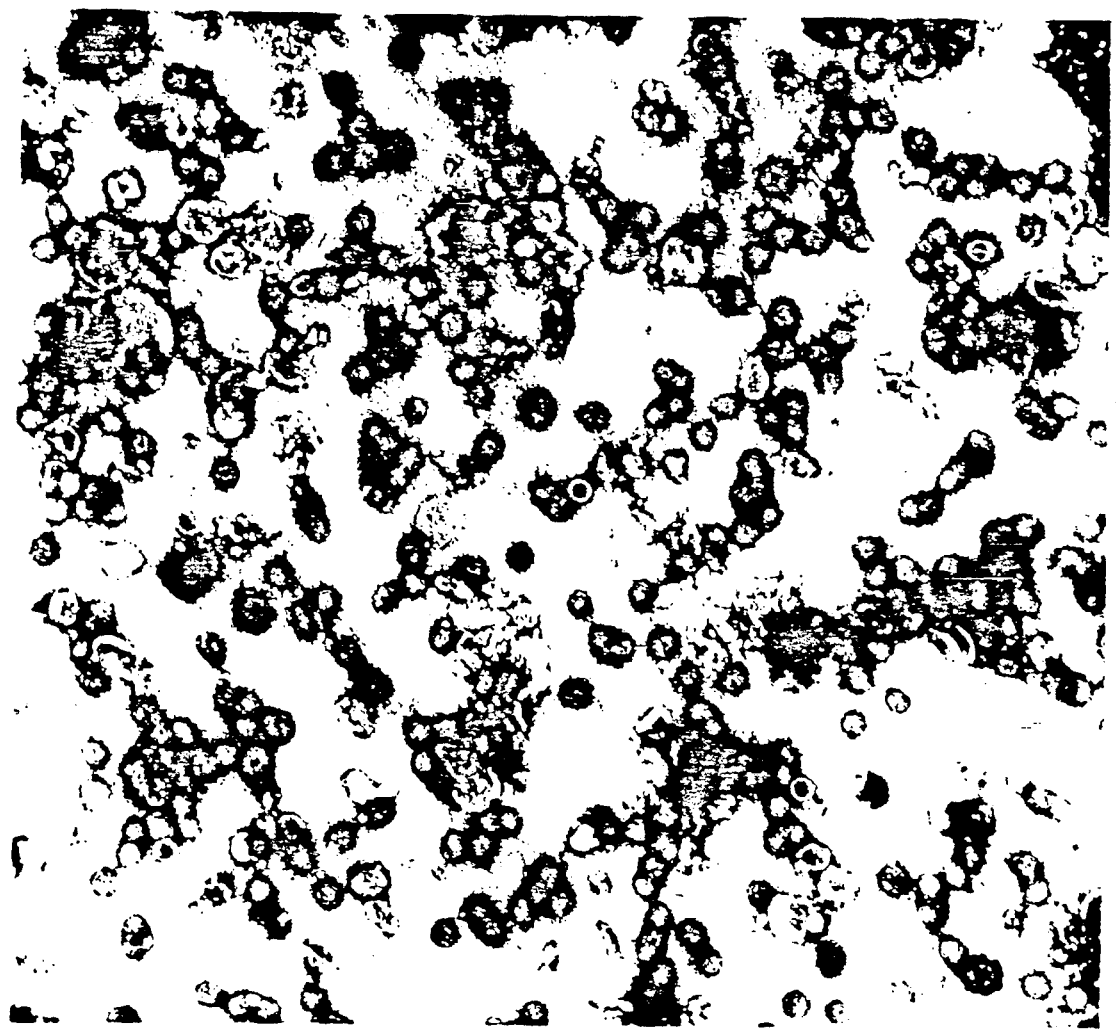

FIG. 12 shows an electron micrograph of purified Ty:HA-VLPs.

Figure 13A:
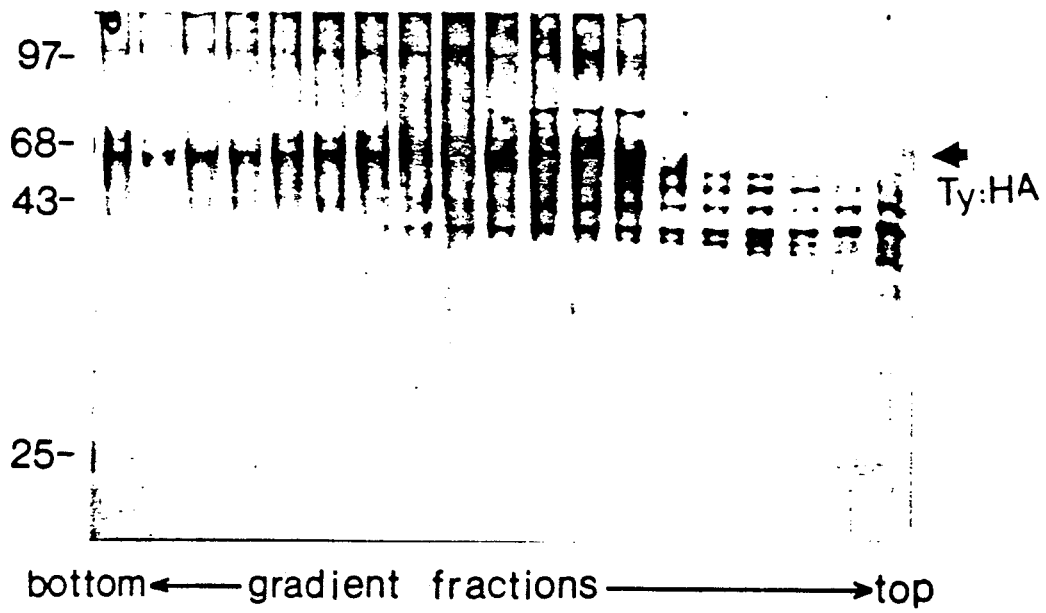
Figure 13B:
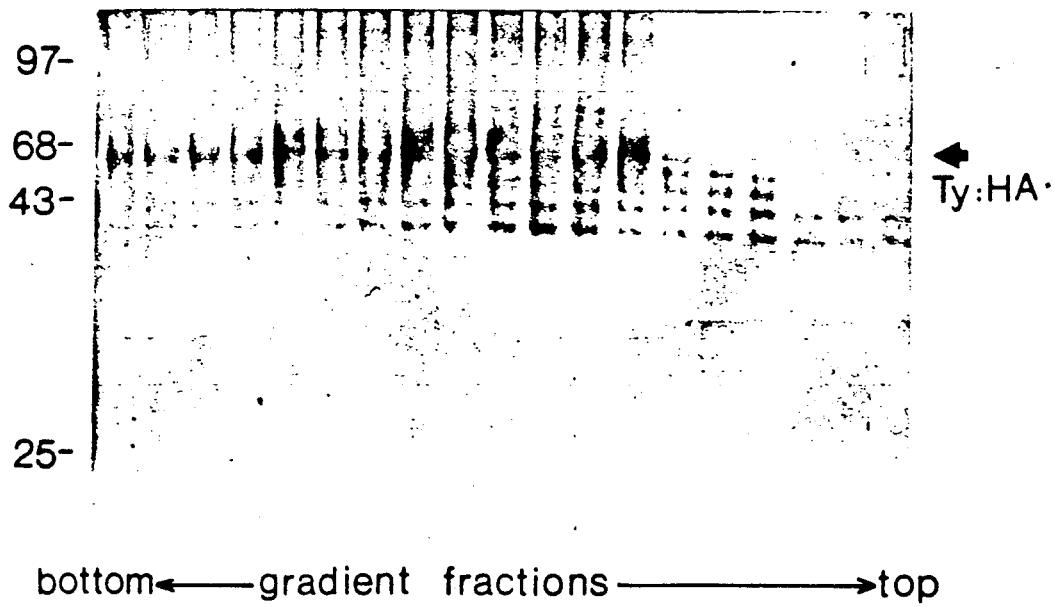

FIG. 13 (A,B) shows Western blots of proteins from sucrose gradient fractions of extracts of MD40-4c transformed with pMA5620-ha23. Blots were probed with anti- Ty-VLP antibody and anti-whole influenza virus antibody.

FIG. 14 (A,B,C,D,E) shows Western blots of purified Ty:HA-VLPs, whole influenza virus NT60 (H3) and whole influenza virus PR8 probed, from left to right, with normal 'pre-bled' rabbit serum, anti-Ty-VLP antiserum, normal 'pre-bled' rabbit serum, anti-Ty:HA-VLP antiserum and anti-whole influenza virus serum.

EXAMPLE 1

Strains used were E.coli AKEC28 (C600, thrC, thyA, trpC1117, hsdRK, hsdK) and S. cerevisiae MD40-4c (urd2, trp1, leu2-3, leu2-112, his3-11, his3-15). E.coli media were prepared according to Miller (Miller 1972 Experiments in Molecular Genetics, CSH p433) and yeast media were prepared according to Hawthorne and Mortimer (Hawthorne and Mortimer 1960 Genetics 45, 1085).

E. coli was transformed using standard methods (Maniatis et al 1982 Molecular Cloning—A Laboratory Manual, CSH p199). Yeast was transformed as described by Hinnen et al (Hinnen et al 1978 Proc. Natl. Acad. Sci. 75, 1929).

Standard procedures were used for restriction digestion and plasmid constructions (Maniatis et al 1982 op. cit). Restriction enzymes and T4 DNA ligase were used according to the suppliers instructions. Bal 31 exonuclease digestions were carried out as described by Dobson et al (Dobson et al 1982 Nucl. Acids Res. 10, 5463). Deletion end points were determined by DNA sequencing (Sanger et al 1977 Proc. Natl. Acad. Sci. 74, 5463). BamHI synthetic oligonucleotide linkers were obtained from Pharmacia.

Plasmid DNA was isolated from E. coli preparatively as described by Chinault and Carbon (Chinault and Carbon 1979 Gene 5, 111) and for rapid analysis by the method of Holmes and Quigley (Holmes and Quigley 1981 Anal. Biochem. 114, 193).

Ty-VLPs were purified as follows. Yeast cells were grown selectively at 30° C. to a density of $8 \times 10^6$ cells.ml$^{-1}$. The cells were then collected by low speed centrifugation, washed once in ice-cold water and resuspended in TEN buffer (10mM Tris, pH 7.4; 2 mM EDTA; 140 mM NaCl) at 1ml per 1 litre of cells. The cells were disrupted by vortexing with glass beads (40-mesh; BDH) at 4° C. until >70% were broken. The beads were pelleted by low speed centrifugation, then the supernatant was collected and the debris removed by centrifugation in a microfuge for 20 minutes. The Ty-VLPs were then pelleted from the supernatant by centrifugation at 100,000g for 1 hour at 4° C. and by resuspended overnight in TEN buffer. The resuspended Ty-VLPs were centrifuged in a microfuge for 15 minutes at 4° C. to remove cell debris prior to loading the supernatant onto a 15–45% (w/v) sucrose gradient in 10 mM Tris, pH 7.4; 10 nM NaCl and spinning at 76,300g for 3 hours at 15° C. Fractions were collected through the bottom of the tube and the peak were collected through the bottom of the tube and the peak fractions were identified by running aliquots of the fractions on SDS-PAGE gels and Coomassie blue staining. VLPs were concentrated by centrifugation of the peak fractions at 100,000 g for 1 hour at 4° C.

Protein extracts of whole yeast cells were prepared as previously described (Mellor et al 1983 Gene 24, 1). Gel procedures were those of Laemmli (Laemmll 1970 Nature 227, 68). Protein concentrations were measured by a dye-binding assay (Bradford 1976 Anal. Biochem. 72, 248) obtained from Bio-Rad Laboratories.

A polyclonal horse anti-interferon(IFN)-alpha antibody was purchased from Boehringer Mannheim. Anti-Ty-VLP antisera were prepared in rabbits by standard procedures.

Western blotting was carried out as described by Towbin et al (Towbin et al 1979 Proc. Natl. Acad. Sci. 76, 4350). Bound antibody was detected using either a rabbit anti-horse second antibody conjugated to horseradish peroxidase (Miles Scientific) or a goat anti-rabbit second antibody followed by a peroxidase-anti-peroxidase (PAP) complex raised in rabbit (sigma). The enzymatic reaction was developed as described by de Blas and Cherwinski (De Blas and Cherwinski 1983 Anal. Biochem. 133, 214).

Plasmid, pMA91-11, has been described previously (Dobson et al 1984 EMBO.J. 3, 1115): it contains the first 1450 nucleotides of the major transcriptional unit of the Ty element, Ty1-15, inserted into the high efficiency expression vector pMA91 (Mellor et al 1983 op. cit; Kingsman and Kingsman 1985 Biotech. and Genet. Eng. Rev. 3, 377). The Ty component was derived from pKT40b as described by Dobson et al (op. cit); pKT40b has been deposited with the National Collection of Industrial Bacteria, Aberdeen, U.K. under accession number NCIB 12427. In turn, the expression vector pMA91 consists of plasmid pBR322 sequences which allow replication and selection in *E. coli*, the yeast 2 micron plasmid origin of replication, which allows efficient autonomous replication in yeast, the yeast LEU2 gene as a selectable marker in both yeast leu2 and *E. coli* leuB mutants and a Bg/II expression site which separates the upstream non-coding region of the yeast PGK gene from −1500 to −1 from the 3' region of PGK which contains all the signals for yeast transcription termination. Plasmid pMA91 is also described in U.S. Pat. No. 4,615,974, although it should be carefully noted that the plasmid designated as pMA3013 in FIG. 15 of this U.S. patent is what is now known as plasmid pMA91. The plasmid shown in the lower part of FIG. 1 of U.S. Pat. No. 4,615,974 has since been renamed.

Figure 1:
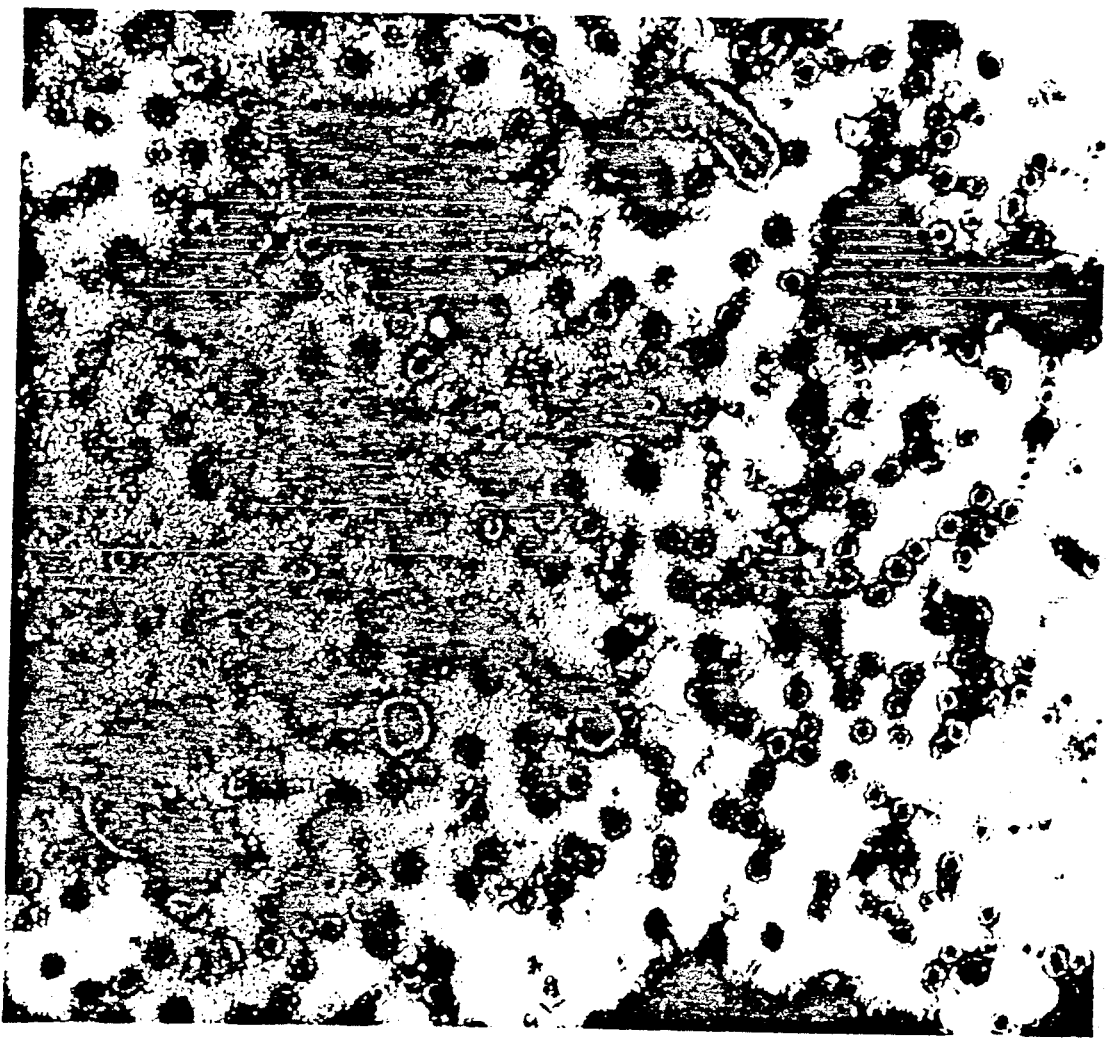
FIG. 1 is a photograph of Ty virus-like particles (Ty-VLPs) purified from MD40-4c transformed with plasmid pMA91-11.
Figure 4A:
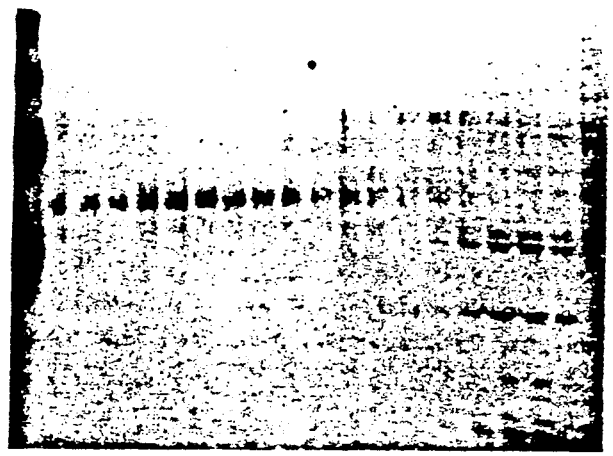
FIG. 4 (A,B,C) shows photographs of SDS-polyacrylamide gel analyses of fractions from a sucrose gradient separation of particles and proteins from MD40-4c containing pMA91-11, pMA91 and pMA5620-8.
Figure 4B:
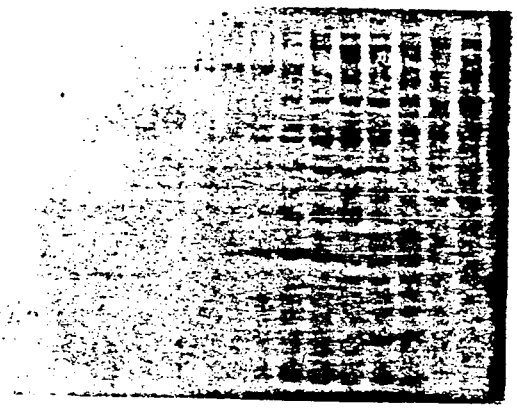
Figure 4C:
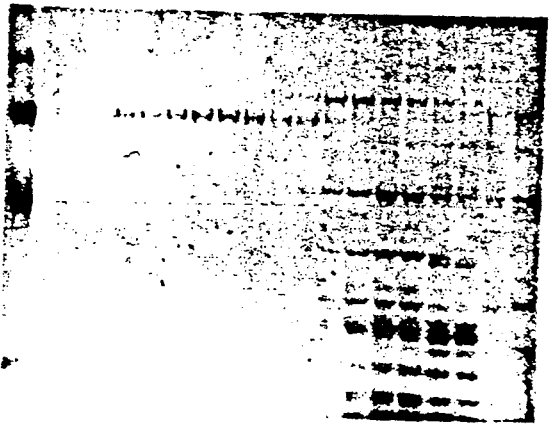

Ty expression is driven, therefore, from the promoter of the highly efficient yeast phosphoglycerate kinase gene (PGK) and yeast extracts of strains containing pMA91-11 overproduce massive amounts of pl protein, the primary translation product of the TYA gene (Dobson et al 1984 op. cit; Mellor et al 1985a op. cit). We now demonstrate that extracts of yeast transformants containing pMA91-11 contain Ty-VLPs in large quantities (FIG. 1). Therefore, TYA alone contains sufficient information to make Ty-VLPs and the pl protein found in extracts of MD40-4c containing pMA91-11 is assembled into particles (FIGS. 1 and 4). This information provides the basis for the present invention.

Figure 2:
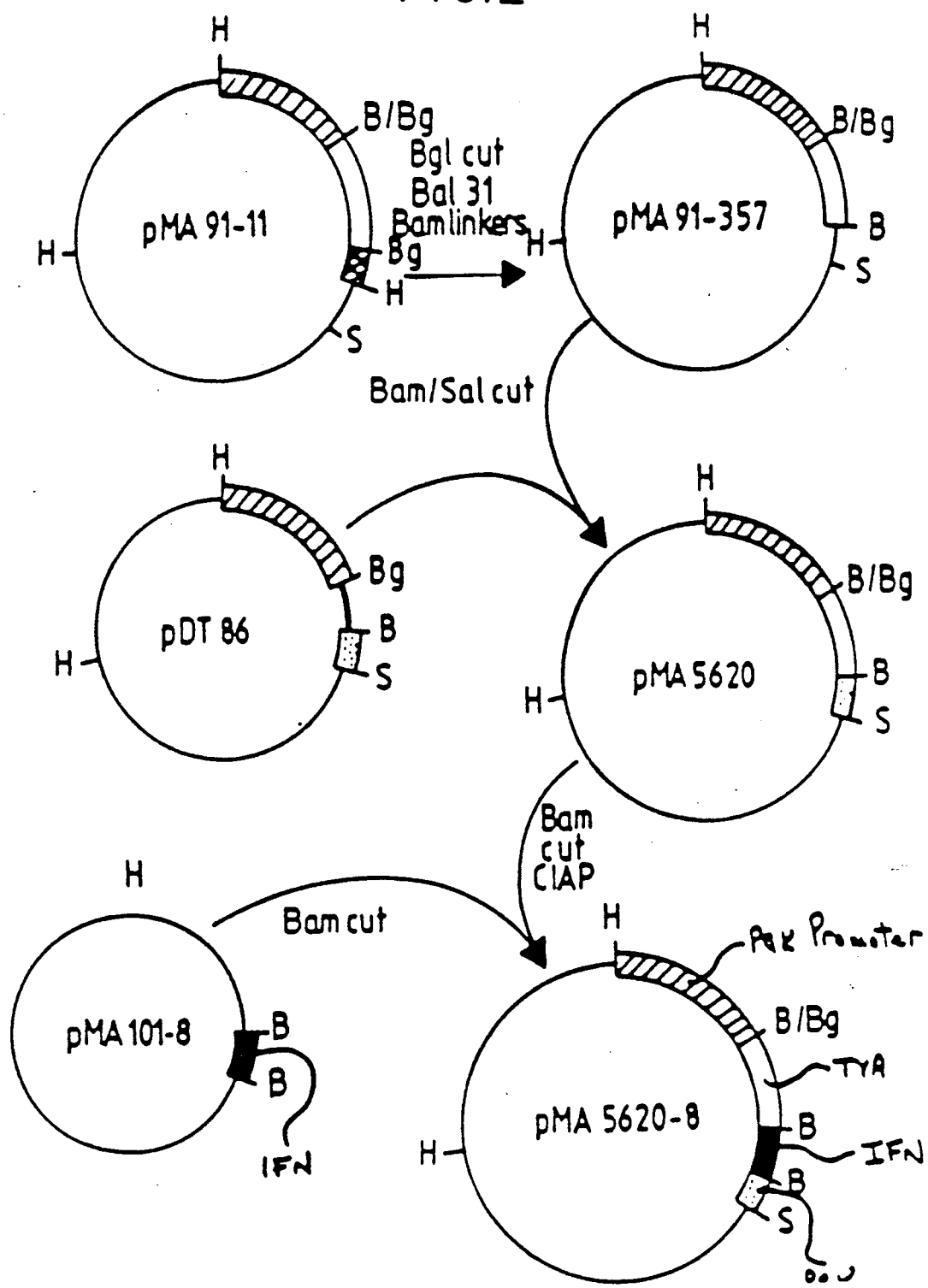
FIG. 2 is a schematic diagram of the construction of pMA5620 and pMA5620-8.

The construction of a plasmid vector, pMA5620, that would direct the synthesis of any hybrid Ty-VLP particle is shown schematically in FIG. 2. This required the construction of a vector containing a convenient restriction endonuclease site within the TYA gene such that any coding sequence can be inserted into that site to create a TYA hybrid gene. However, it is essential that within such a hybrid there is sufficient TYA coding sequence to direct the synthesis of Ty-VLPs.

Figure 3:
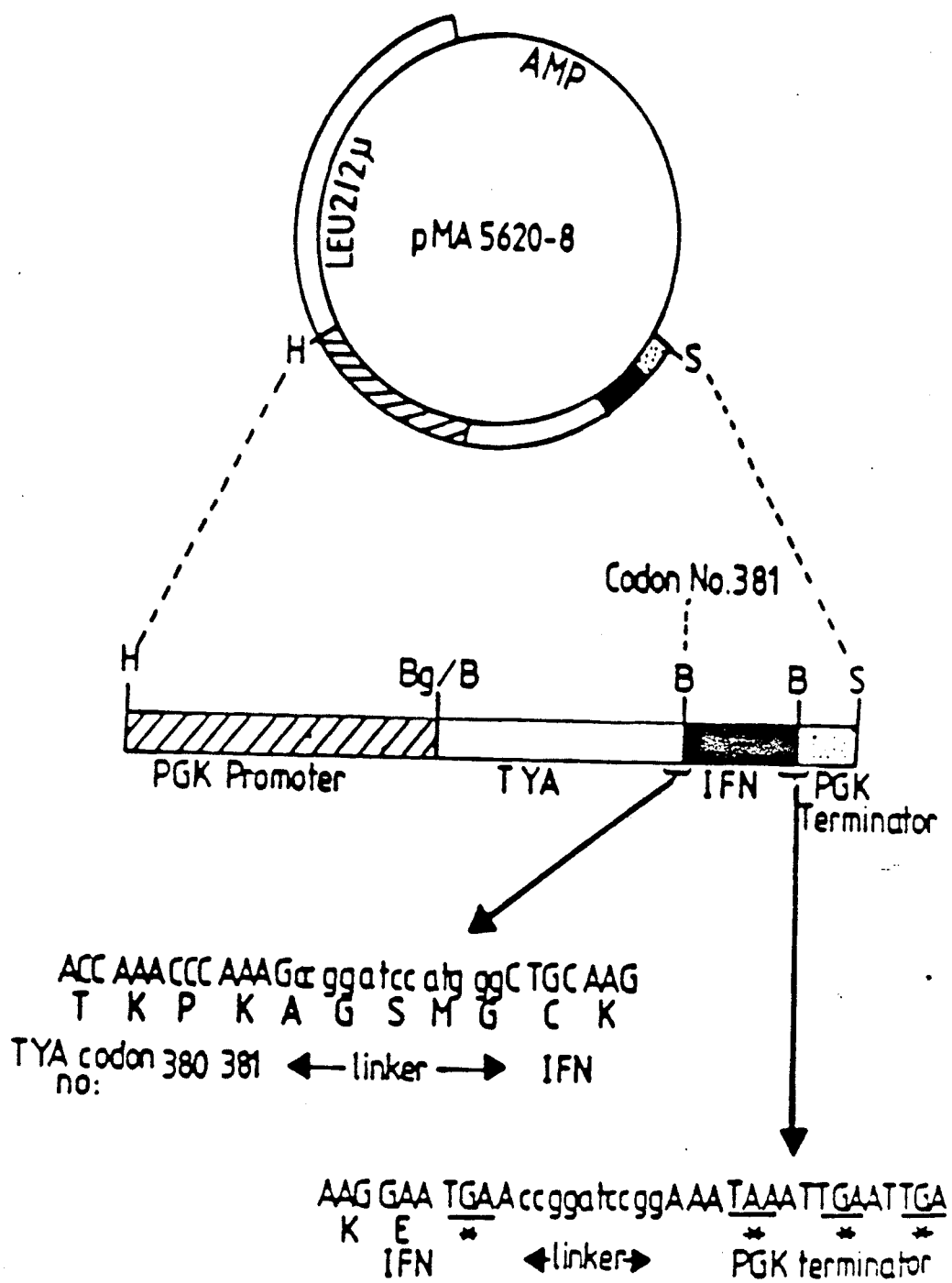
FIG. 3 is a schematic diagram of plasmid pMA5620-8, with an expanded diagram of the key components of this example of the invention and the nucleotide sequences of key junctions.

Plasmid pMA91-11 was cleaved with BglII, digested with Bal 31 exonuclease for various times and re-ligated in the presence of excess Bam HI linkers (CCGGATCCGG). The deletion end points of the resulting plasmids were determined by DNA sequencing. Plasmid pMA91-357 is a deletion derivative in which 265 bp have been removed. This places the BamHI linker one nucleotide beyond codon 381 of TYA (FIG. 3).

In order to provide both transcription termination sequences and translation stop codons in all three reading frames the deleted PGK 3' terminator sequences of pMA91-357 were replaced with a 287 bp BamHI-SalI DNA fragment isolated from plasmid pDT86. This DNA fragment is a modified 3' transcription terminator fragment from the yeast PGK gene which contains translation stop codons in all three reading frames downstream of the BamHI site (FIGS. 2 and 3). This terminator fragment starts with a BamHI linker (CCGGATCCGG) linked to the last sense codon of the PGK coding sequence and extends to the HindIII site 279 nucleotides beyond the PGK coding sequence (Hitzeman et al 1982 Nucl. Acids Res. 10, 7791). In these constructions the HindIII site has been converted to a SalI site using a synthetic linker. The terminator fragment is not critical and any fragment containing termination codons in all three reading frames followed by a yeast transcription terminator would suffice. The resulting plasmid, pMA5620, contains a unique BamHI site into which any suitable sequence can be inserted to produce a hybrid protein which will be assembled into hybrid Ty-VLPs.

In order to test pMA5620 an interferon alpha2 (IFN) cDNA was used as a model antigen coding sequence. A 540 bp BamHI IFN-alpha2 cDNA fragment, designated fragment 8 (Mellor et al 1985 b Gene 33, 215) was inserted into the unique BamHI site of plasmid pMA5620. The resulting plasmid is designated pMA5620-8 (FIGS. 2 and 3).

Figure 5:
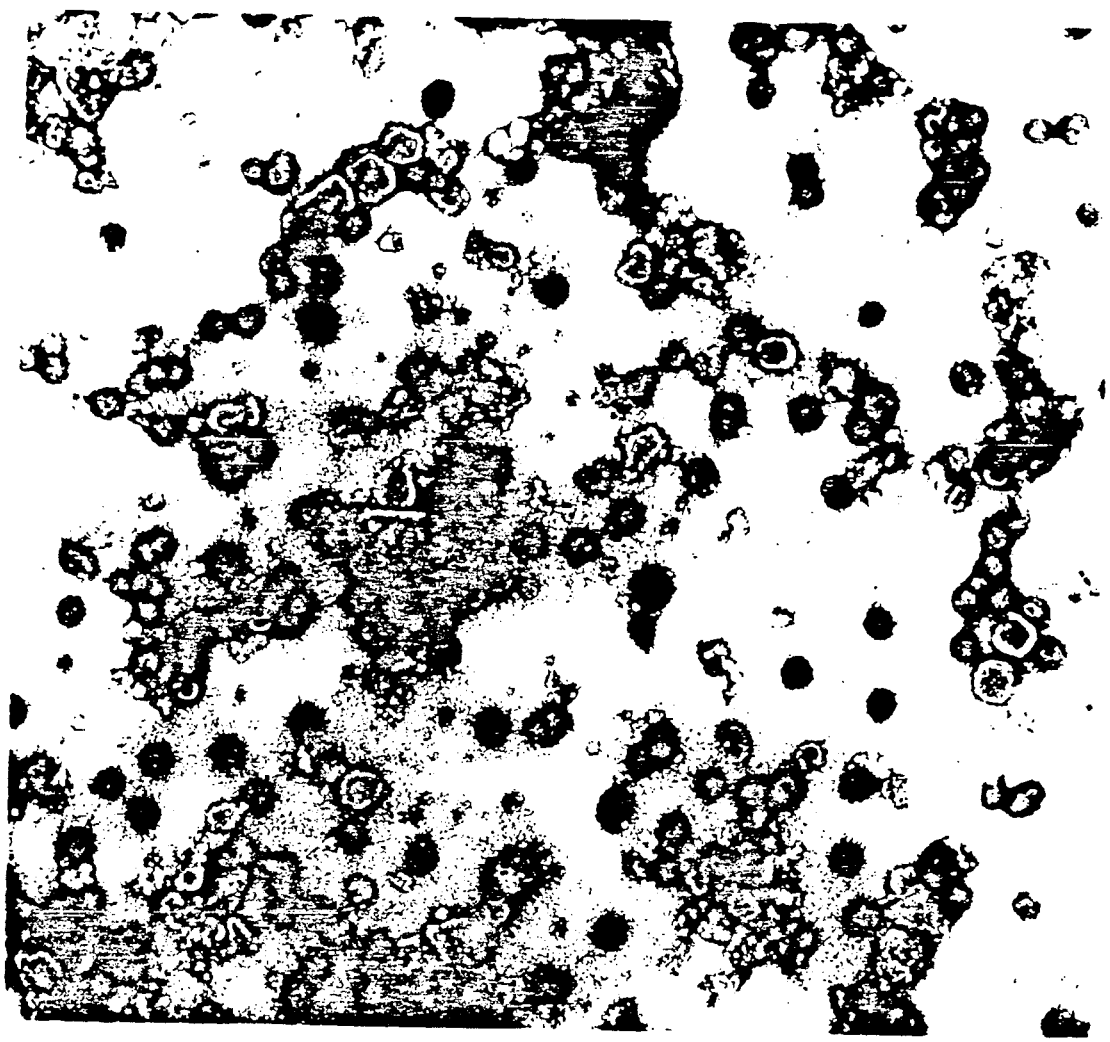
FIG. 5 is a photograph of hybrid Ty:IFN-VLPs purified from MD40-4c containing pMA5620-8.

VLPs were prepared from yeast strain MD40-4c transformed with plasmid pMA5620-8 and fractions from a 15–45% sucrose gradient were run on an SDS-PAGE gel. The proteins in the gradient were visualised by Coomassie Blue staining (FIG. 4). The position in the gradient of the predicted 70 kd TYA-IFN fusion protein demonstrated conclusively the particulate nature of the protein. Electron microscopy of the fractions confirmed that particles were present (FIG. 5). In order to establish that this 70 kd particulate protein was indeed a Ty(50kd):IFN(20kd) fusion protein, fractions fromsucrose gradients were again run on SDSPAGE gels and the separated proteins were transferred to nitrocellulose filters. One filter was probed with a Ty-VLP antibody known to react with Ty proteins and another was probed with an anti-IFN-alpha antibody (FIG. 6). In both cases the 70 kd protein reacted strongly, indicating that this protein contained both Ty and IFN epitopes.

Figure 7:
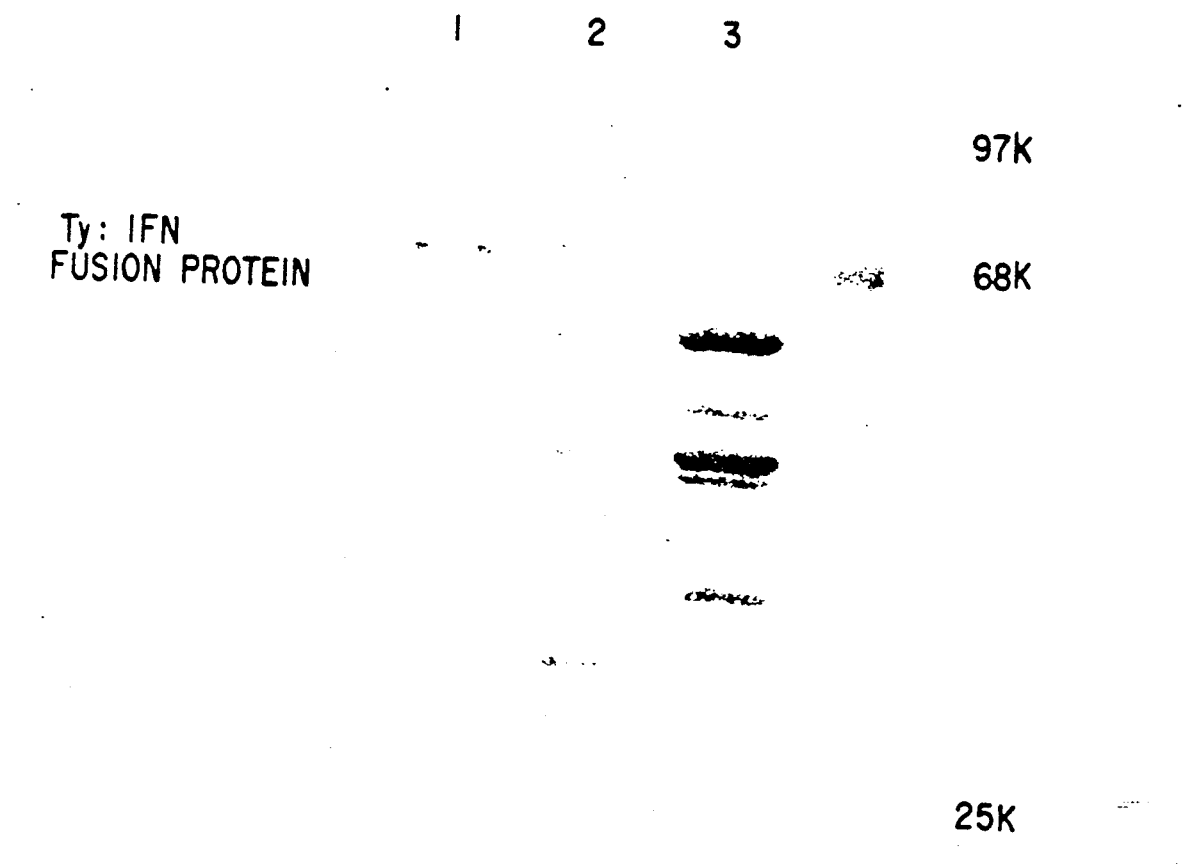

The efficiency of the method for purification of hybrid Ty:IFN-VLPs is illustrated in FIG. 7. The 70 kd hybrid protein is by far the major species in the preparation.

In order to test the efficacy of these hybrid Ty:IFN-VLPs in eliciting an immune response to the model antigen, interferon, an antiserum was raised in rabbits against concentrated hybrid Ty:IFN-VLPs purified from yeast extracts transformed with pMA5620-8. An extract of MD40-4c transformed with plasmid pMA91-1 which overproduces IFN-alpha2 (Mellow et al 1985b op. cit) was run on an SDS-PAGE gel alongside an extract of MD40-4c transformed with pMA91 which produces no interferon. The separated proteins were transferred to nitrocellulose and probed with either Ty-VLP antisera or Ty:IFN-VLP antisera (FIG. 8). Whereas both antisera reacted with Ty proteins present in the extracts only the anti hybrid Ty:IFN-VLP antisera reacted with the 20 kd IFN protein in the extract containing plasmid pMA91-1.

These data show: 1) pMA5620-8 directs the synthesis of a hybrid fusion protein composed of the first 381 amino acids of Ty protein p1 and a non-Ty protein. In this case interferon-alpha2; 2) this fusion protein forms hybrid Ty:IFN-VLPs; 3) the hybrid Ty:IFN-VLPs can be isolated easily; 4) the hybrid Ty:IFN-VLPs present the model antigen, interferon-alpha2, to the rabbit immune system. It is reasonable, therefore, to expect that pMA5620 will direct the synthesis of any hybrid Ty-VLP and that any antigen present in such a particle will be presented to any mammalian immune system eg rat, hamster, dog, cat, cattle, sheep, pigs and human. Clearly the interferon cDNA used as an example here could be replaced with any other piece of DNA that would encode a complete protein or part of a protein.

The particulate nature of this antigen presentation system and the ease with which the hybrid Ty-VLPs can be purified make this invention useful as a means of stimulating the production of antibodies to defined antigens, as a means of creating new vaccines, as a means of preparing defined antigens for monoclonal antibody production, as a means of preparing antigens for use in diagnostic assay methods.

Hybrid Ty:IFN-VLPs can therefore be used to raise anti-IFN antibodies (either monoclonal or polyclonal, but preferably monclonal), which may then be used for the purification of IFN.

EXAMPLE 2

The copia element of *Drosophilia melanogaster* is remarkably similar to the Ty element of yeast in both genetic organisation and virus-like particle formation (Mount & Rubin 1985 Mol. Cell. Biol. 5 1630). The region of copia that is equivalent to TYA is called gag by analogy with retrovirus organisation. Therefore expression at high levels of the gag region of a copia element in an insect cell expression system may be found to lead to proteins which assemble into particles similar to the Ty-VLPs. If the gag is fused to the coding sequence of another protein the resulting fusion protein may also be found to assemble into a hybrid copia particle analogous to the Ty:IFN hybrid particles described above.

In order to establish copia particles as an antigen presentation and purification system gag from plasmid pPW220 (Potter & Brosein 1979 Cell 17 415) is manipulated by standard recombinant DNA procedures for insertion into a typical high efficiency Baculovirus expression vector such as pAc373 (Smith et al 1983 J. Virol. 46, 584) to produce plasmid pAc373-gag. Expression is driven by the polyhedrin promoter. An interferon cDNA is then inserted, in frame, into the 3' end of gag to produce plasmid pAc373-gag-IFN. This plasmid is directly analogous to pMA5620-8 (see Example 1 above). pAc373-gag-IFN is then introduced into the Baculovirus Autographa californica nuclear polyhedrosis virus (AcNPV) by in vivo recombination in *Spodoptera frugiperda* cells (Smith et al 1983 Mol. Cell. Biol. 4 2156). Recombinant viruses are harvested from occlusion-minus plaques and used to reinfect fresh *S. frugiperda* cells. Hybrid copia:IFN particles are harvested at 72–96 hours post-infection and fractionated on a sucrose gradient to separate them from Baculovirus contamination. Particles are identified by electron microscopy and Western blotting as described for Ty:IFN hybrid particles (see Example 1 above).

EXAMPLE 3

The general procedure of Example 2 is followed, except that a recombinant plasmid containing the gag-IFN fusion expressed by the Drosophila ADH gene promoter (Benyajati et al 1983 Cell 33 125) is introduced into any insect cell (eg Drosophila Schneider 2 cells) by simple DNA mediated transfection.

EXAMPLE 4

The TYA gene of the yeast Ty element is directly analogous to the gag genes of avian and mammalian retroviruses. As the product of TYA alone is capable of forming particles it is likely that any gag protein will do the same and could therefore act as the basis for an antigen presentation and purification system.

In order to establish retroviral gag proteins as antigen purification and presentation systems the gag gene from HIV-I is manipulated by standard recombinant DNA procedures to be inserted into the yeast expression vector pMA91 and a derivative of the mammalian expression vector pSV2 (Southern and Berg 1982 J. Mol Appl. Genet. 1 327), which contains a mammalian dhfr cDNA (Kaufman et al 1985 Mol. Cell. Biol. 5 1750), to produce pMA91-HIVgag and pSV25-HIVgag respectively. An interferon cDNA is then inserted, in frame, into both of these molecules at the 3 end of gag to produce pMA91-HIVgag-IFN and pSV25-HIVgag-IFN respectively. These molecules are analogous to pMA5620-8 (see Example 1 above). pMA91-HIVgag-IFN is then used to transform yeast strain MD40-4c and pSV25-HIVgag-IFN is used to transfect CHO dhfr- cells. Stable transformants are propogated and cell extracts prepared and fractionated on sucrose gradients. Hybrid HIVgag:IFN particles are identified by electron microscopy and Western blotting. As described for Ty:IFN hybrid particles (see Example 1 above).

EXAMPLE 5

The procedure of Example 4 is followed, except that pSV25-HIVgag-IFN is introduced into COS cells (Gluzman et al 1977 J. Virol. 24 534) and hybrid particles are harvested between 3 and 9 days post transfection.

EXAMPLE 6

In this example we demonstrate that hybrid Ty-VLPs containing part of an influenza virus haemagglutinin (HA) can be produced and that these hybrid Ty:HA- VLPs induce the formation of anti-HA antibodies in rabbits.

The strategy for these experiments was essentially the same as for the production and analyses of the hydrid Ty:IFN-VLPs described in Example 1. MRC12/80 antiwhole influenza virus antibody was obtained from the World Influenza Centre at NIMR, Mill Hill, U.K. and was raised against influenza virus strain A/Scotland/840/74 ×A/PR/8/34 (H3N2). A region of the HA coding sequence corresponding to codons 25-111 of the HA1 domain of influenza virus A/Memphis/102/72 (H3N2) was chosen for the formation of hybrid Ty:HA-VLPs on the basis of the data of Wilson et al (1984 Cell 37, 767). A 262 bp SpeI:SpeI (FIG. 9), corresponding to codons 25-111, was purified from an appropriate digest of plasmid MX29. MX29 is plasmid pAT153 (Twigg and Sherratt, 1980 Nature 283, 216) with an H3 HA cDNA derived from the HA RNA from influenza virus strain A/Memphis/102/72 G:C tailed into the PstI site. The sticky-ends of the SpeI:SpeI fragment were filled-in using DNA polymerase I and then the fragment was blunt-end ligated into the HincII site of plasmid pSP46 to produce pSP46-ha23. pSP46 is a derivative of pSP64 (Promega Biotec) in which the HindIII site of pSP64 has been converted into a BglII site. A BamHI:BglII fragment, designated ha23, was purified from pSP46-ha23. ha23 contains the filled-in 262 bp SpeI:SpeI fragment. ha23 was then inserted into the BamHI site of pMA5620 to produce pMA5620-ha23 (FIG. 10). This plasmid was then used to transform yeast strain MD40-4c to leucine independence.

VLPs were prepared from yeast strain MD40-4c transformed with pMA5620-ha23 or pMA5620 and fractionated on a 15-45% sucrose gradient. Fractions were run on an SDS-PAGE gel and proteins were visualised with Coomassie blue (FIG. 11). The position in the gradient of the predicted TYA-HA fusion protein demonstrated the particulate nature of the protein. Electron microscopy of the fractions confirmed that particles were present. (FIG. 12).

In order to confirm that the particles contained HA antigens fractionated extracts of MD40-4c containing pMA5620-ha23 from similar gradients were again run on SDS-PAGE gels and the separated proteins were electroblotted to nitrocellulose filters. One filter was probed with anti-Ty-VLP antibody known to react with Ty proteins and another was probed with anti-HA antibody. In both cases the the putative Ty:HA fusion protein reacted strongly indicating that this protein contained both Ty and HA epitopes (FIG. 13).

In order to test the efficacy of these hybrid Ty:HA-VLPs in eliciting an immune response to HA an antiserum was raised in rabbits against concentrated hybrid Ty:HA-VLPs purified from extracts of MD40-4c transformed with pMA5620-ha23. This antiserum was then used to probe proteins from disrupted whole influenza virus by Western blotting. Three protein samples were used. The first was purified Ty:HA-VLPs used to raise the antiserum. The second was whole influenza virus PR8 (H3). The third was whole influenza virus NT60 (H1). Both PR8 and NT60 were obtained from Professor George Brownlee, Sir William Dunn School of Pathology, Oxford, U.K. H1 HA and H3 HA should not cross react in immunological assays using antibody raised against the amino acid 25-111 region (Webster et al 1983 in "Genetics of Influenza Viruses"—Palese & Kingsbury (Eds.) Springer-Verlag p127). FIG. 14 shows that the anti-Ty:HA-VLP antibody reacts with the HA1 region of the H3 HA but not with the H1 HA. No such reaction is seen with pre-bled serum nor with anti-Ty-VLP antibody. As a positive control the same samples were probed with anti-whole virus antibody. In this case both H1 HA and H3 HA reacted with the antiserum. We can conclude that the hybrid Ty:HA-VLPs induce the production of anti-HA antibody specific for an epitope of the H3 antigen.

These data show that pMA5620-ha23 directs the synthesis of a hybrid fusion protein composed of the first 381 amino acids of Ty protein p1 and a small region of a viral protein, influenza virus HA. This fusion protein forms hybrid Ty:HA-VLPs. The hybrid Ty:HA-VLPs can be isolated easily and present the small HA component to the rabbit immune system in such a way that anti-HA antibodies are produced. These antibodies can distinguish between H1 HA and H3 HA. Clearly the HA component of the hybrid Ty:HA-VLPs could be replaced with any other influenza virus component or any other virus component and it is reasonable to expect that similar results would be obtained.

What is claimed is:

1. A DNA sequence comprising a yeast YA gene coding sequence in a single reading frame with a coding sequence for an antigen, wherein the yeast TYA gene and antigen coding sequences encode a particle-forming fusion protein.

2. An expression vector comprising a DNA sequence which is a yeast TYA gene coding sequence in a single reading frame with a coding sequence for an antigen wherein the expression vector expresses a particle-forming fusion protein encoded by the yeast TYA gene and antigen coding sequences.

* * * * *

UNITED STATES PATENT AND TRADEMARK OFFICE
CERTIFICATE OF CORRECTION

PATENT NO. : 5,041,385
DATED : August 20, 1991
INVENTOR(S) : Alan J. Kingsman, Susan M. Kingsman, Sally E. Adams, Michael H. Malim, Elizabeth-Jane C. Mellor It is certified that error appears in the above-identified patent and that said Letters Patent is hereby corrected as shown below:

Column 3, lines 3 and 4, "Human Immunodeficiency Virus I and II" should read --Human Immunodeficiency Virus 1 and 2--
Column 3, line 4, "(HIV-I, HIV-II)" should read --(HIV-1, HIV-2)--
Column 3, line 57, "HIV-I or HIV-II" should read --HIV-1 or HIV-2--
Column 6, line 26, "urd2" should read --ura2--
Column 6, line 53, "8 x 106" should read --$8 \times 10^6$--
Column 7, line 1, "10nM" should read --10mM--
Column 7, lines 3 and 4, delete "and the peak were collected through the bottom of the tube."
Column 7, line 25, "(sigma)" should read --(Sigma)--
Column 7, line 46, "Bg/II" should read --BgI--
Column 10, line 55 "blotting. As" should read --blotting as--
Claim 1, Column 12, line 41, "YA" should read --TYA--

Signed and Sealed this

Fifth Day of October, 1993

Attest:

BRUCE LEHMAN

*Attesting Officer*     *Commissioner of Patents and Trademarks*